United States Patent [19]

Monchalin

[11] Patent Number: 4,966,459
[45] Date of Patent: Oct. 30, 1990

[54] BROADBAND OPTICAL DETECTION OF TRANSIENT MOTION FROM A SCATTERING SURFACE

[75] Inventor: Jean-Pierre Monchalin, Montreal, Canada

[73] Assignee: Canadian Patents and Development Limited-Societe Canadienne des Brevets et d'Exploitation Limitee, Canada

[21] Appl. No.: 310,380

[22] Filed: Feb. 15, 1989

[30] Foreign Application Priority Data

Apr. 29, 1988 [CA] Canada .................................. 565550

[51] Int. Cl.[5] ............................................. G01B 9/02
[52] U.S. Cl. .................................... 356/358; 356/352; 73/657
[58] Field of Search ............... 356/352, 354, 355, 356, 356/358; 73/655, 657

[56] References Cited

U.S. PATENT DOCUMENTS

| | | | |
|---|---|---|---|
| 4,046,477 | 9/1977 | Kaule | 356/358 |
| 4,129,041 | 12/1978 | Bickel | 73/657 |
| 4,388,832 | 6/1983 | Kaule | 73/655 |
| 4,633,715 | 1/1987 | Monchalin | 356/358 |
| 4,659,224 | 4/1987 | Monchalin | 356/352 |

OTHER PUBLICATIONS

R. W. P. Drever et al., Applied Physics B, vol. 31, (1983), pp. 97–105.

Primary Examiner—Vincent P. McGraw
Assistant Examiner—S. A. Turner
Attorney, Agent, or Firm—Foley & Lardner, Schwartz, Jeffery, Schwaab, Mack, Blumenthal & Evans

[57] ABSTRACT

A method and apparatus for optically detecting transient motion from a scattering surface. A laser beam having a predetermined frequency is directed onto such a surface to thereby scatter the laser beam and produce a scattered laser beam defining an optical wavefront and having an optical spectrum with a central peak at the laser frequency and a sideband on either side of the central peak. The laser beam scattered by the surface is caused to interfere with a reference beam derived from the scattered beam and having an optical wavefront substantially matching the wavefront of the scattered beam and an optical spectrum with a single peak at the laser frequency and no sidebands, to obtain an optical signal which is detected and converted into an electrical signal representative of the transient motion. The optical detection technique according to the invention has a broad frequency bandwidth and a large étendue providing greater sensitivity of detection, and is particularly useful for detecting small surface deformations of a material or workpiece subjected to ultrasonic energy.

25 Claims, 3 Drawing Sheets

BROADBAND OPTICAL DETECTION OF TRANSIENT MOTION FROM A SCATTERING SURFACE

BACKGROUND OF THE INVENTION

The present invention relates to a method and apparatus for optically detecting transient motion from a scattering surface. The invention is particularly directed toward detecting optical phase modulations such as those produced by ultrasound.

The detection of the phase modulation or frequency modulation of an optical wave is important for various fields of application where optical beams are used to detect the motion of objects. This is the case of laser sensing of vibrations and laser detection of ultrasound and of transient body deformations such as those produced by a shock or on impact. Of particular interest for practical applications is the case where ultrasound or a shock wave is generated by a laser. In this case, a completely remote ultrasonic inspection system can be realised, permitting for example ultrasonic probing at elevated temperatures. A technique based on laser generation and optical detection can thus be advantageously used to inspect materials at high temperatures (such as all metals and ceramics) for process and quality control, to detect flaws as soon as they are created during processing, to measure production parameters (thickness, temperature, etc.) and to determine microstructural properties on-line (grain size, porosity, etc.).

Ultrasound is generally produced by a high power laser which heats locally the surface of a sample or workpiece to produce an acoustic source, and the phase or frequency modulation can be detected by means of a laser interferometer. Since in many cases, the modulation excursions to be detected are small, sensitivity is a prime concern. Adequate sensitivity requires a receiving demodulating means which has a large effective light gathering efficiency. The poor sensitivity of most of the optical detection systems known to date is one of the main reasons that has limited the practical evolution of such a technology to full commercial application.

Generally, the light gathering efficiency of an interferometric system is characterized by its étendue parameter (or throughput), defined as the product of its effective entrance aperture area by the solid angle limited by the rays of maximum inclination passing through the entrance aperture center and thus defining the field of view. The maximum inclination rays can be defined as those which produce a shift of the interference pattern by a quarter of a fringe. The importance of this étendue parameter stems from its invariance within the frame of geometrical optics. A large étendue permits to choose light collecting optics of large size, being only limited by cost and practical feasibility, and to detect surface motion over a large area.

Also of prime concern for many applications is the capability of providing a frequency response representative of the exact surface motion. This can only be achieved if the detecting technique has a broad frequency bandwidth.

The effect of transient motion upon a laser beam scattered by a surface can be described in three different and equivalent ways. It can be said that the surface motion produces a variable phase shift or a Doppler shift of the instantaneous frequency, or generates sidebands on both sides of the laser frequency. In the case of pulsed ultrasonic excitation, these sidebands are broadened.

Applicant has already described in U.S. Pat. No. 4,633,715 a laser heterodyne interferometric method and system for measuring ultrasonic displacements, based on causing interference of the laser beam scattered by the surface of a workpiece with a reference beam originating from the same laser source, the frequency of the reference beam being shifted by means of a Bragg or acoustooptic cell. Since in this method, the reference wave is directly derived from the laser, its wavefront does not match the wavefront of the beam scattered by the surface. This has the drawback of causing sensitivity to speckles and a very limited étendue. Best detectivity is obtained when approximately on speckle is detected, which requires focusing the beam onto the workpiece surface. Sensitivity is very variable depending on the intensity of the speckle which overlaps the reference beam.

The use of a two-wave interferometer has also been proposed in U.S. Pat. No. 4,046,477 to W. Kaule, for sensing surface deformation of a workpiece subjected to ultrasonic energy. The optical Doppler shift produced in a laser beam scattered by the surface of the workpiece is detected by means of a Michelson-type interferometer. Since a long optical path difference is needed for a Michelson interferometer to have adequate frequency discriminatory sensitivity and the central fringes of interference are thus viewed under a very small angle, the interferometer proposed by Kaule has a very limited étendue when the surface being observed is not mirror-like.

In order to provide a discriminating system having a large étendue or light gathering efficiency, Applicant has proposed in U.S. Pat. No. 4,659,224 to use an optical interferometer of the confocal Fabry-Perot type The advantages of such an interferometric system are its unsensitivity to speckles and its large light gathering efficiency. However, being based on a filtering action, its frequency bandwidth is consequently limited and its response cannot be flat over a large frequency span.

SUMMARY OF THE INVENTION

It is therefore an object of the present invention to overcome the above drawbacks and to provide a method and apparatus for optically detecting transient motion from a scattering surface, having a large étendue or light gathering efficiency as well as a broad frequency bandwidth.

According to one aspect of the invention, there is thus provided a method of optically detecting transient motion from a scattering surface, which comprises directing a laser beam having a predetermined frequency onto such a surface to thereby scatter the laser beam and produce a scattered laser beam defining an optical wavefront and having an optical spectrum with a central peak at the laser frequency and a sideband on either side of the central peak. The laser beam scattered by the surface is caused to interfere with a reference beam derived from the scattered laser beam and having an optical wavefront substantially matching the wavefront of the scattered beam and an optical spectrum with a single peak at the laser frequency and no sidebands, to obtain an optical signal which is detected and converted into an electrical signal representative of the transient motion.

The present invention also provides, in another aspect thereof, an apparatus for optically detecting transient motion from a scattering surface, which comprises:

laser source means for generating a laser beam having a predetermined frequency and directing same onto the aforesaid surface to thereby scatter the laser beam and produce a scattered laser beam defining an optical wavefront and having an optical spectrum with a central peak at the laser frequency and a sideband on either side of the central peak;

optical assembly means for deriving from the scattered laser beam a reference beam having an optical wavefront substantially matching the wave front of the scattered beam and an optical spectrum with a single peak at the laser frequency and no sidebands, and for causing the scattered laser beam to interfere with the reference beam so as to obtain an optical signal; and detector means for detecting the optical signal and converting same into an electrical signal representative of the transient motion.

Applicant has found quite unexpectedly that by deriving from the laser beam scattered by the surface a reference beam having a wavefront matching the wavefront of the scattered beam and causing this reference beam, after stripping it from its sidebands, to interfere with the scattered laser beam whose frequency spectrum includes the carrier laser frequency and adjacent sidebands, transient motion will be detected with a large étendue or light gathering efficiency and a broad frequency bandwidth.

By the expression "transient motion" is meant a motion having non-zero acceleration. Such an expression thus includes all oscillating motions, but excludes motions of constant velocities.

The invention is particularly useful for detecting small surface deformations or displacements of a material subjected to ultrasonic energy, enabling displacements ranging from a fraction of 1Å to a few hundred Å to be detected with a large étendue or light gathering efficiency and a broad frequency bandwidth.

BRIEF DESCRIPTION OF THE DRAWINGS

Further features and advantages of the invention will become more readily apparent from the following description of preferred embodiments as illustrated by way of examples in the accompanying drawings, in which.

DESCRIPTION OF PREFERRED EMBODIMENTS

Figure 1:
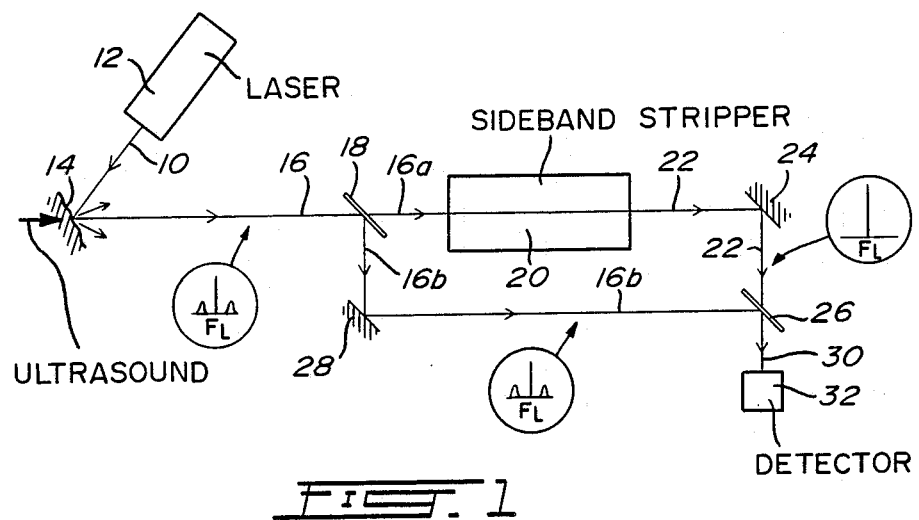
FIG. 1 is a schematic diagram illustrating the principle on which the present invention is based.

Referring first to FIG. 1, a laser beam 10 generated by the laser source 12 is directed onto the surface 14 of a material or workpiece subjected to ultrasonic energy. The ultrasonic displacement of the surface 14 probed by the laser beam 10 can be produced by an ultrasonic piezoelectric transducer or other means such as electrical discharge, projectile impact or high intensity laser pulse; it can also occur naturally in a strained material. As the laser beam 10 impinges on the surface 14, it is scattered by the surface, the scattered laser beam 16 thus produced having an optical spectrum with a central peak at the laser frequency $F_L$ and a sideband on either side of the central peak, as shown in the insert. The scattered beam 16 is divided by means of a beam splitter 18 into two beam portions 16a and 16b, the beam portion 16b serving as a mesuring beam. The beam portion 16a is sent through a sideband stripper 20 so as to strip it from its sidebands and thereby provide a reference beam 22 having an optical spectrum with only a single peak at the laser frequency $F_L$ and no sidebands. The reference beam 22 emerging from the sideband stripper 20 is reflected by a mirror 24 onto a beam mixer 26 where it is combined with the measuring beam 16b which is reflected by the mirror 28 onto the beam mixer 26, the combined beams 30 interferring with one another to produce an optical signal which is detected by the photodetector 32 and converted into an electrical signal representative of the surface displacement. Since the reference beam 22 is derived from the scattered laser beam 16 and use is made of a sideband stripper 20 of appropriate design, the wavefront of reference beam 22 substantially matches the wavefront of the scattered beam 16 so that a large étendue or light gathering efficiency is obtained. On the other hand, using for interference a reference beam 22 which comprises no frequency other than the carrier laser frequency enables to obtain a broad frequency bandwidth.

Figure 2:
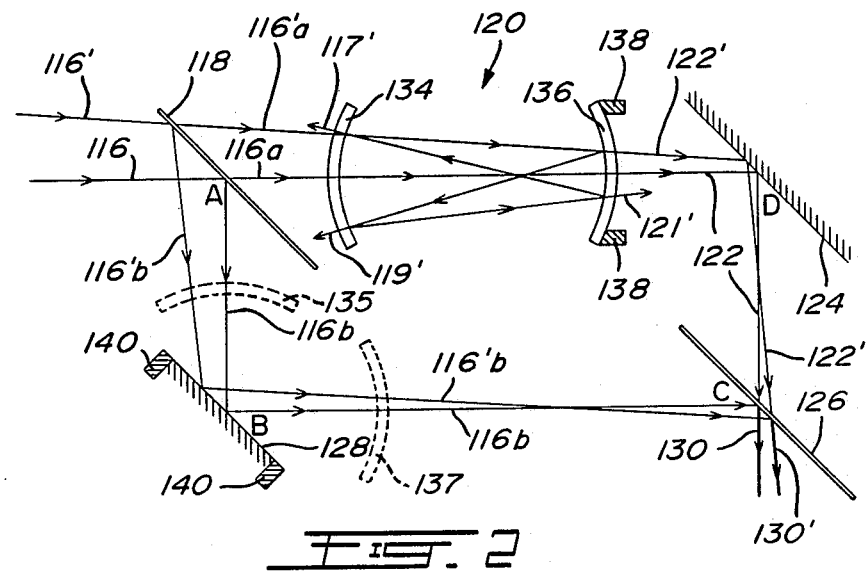
FIG. 2 is another schematic diagram illustrating the use of a confocal cavity in transmission mode as a sideband stripper, the confocal cavity being optically coupled with a two-wave interferometer of Mach-Zehnder type configuration.

In order to be useful, the sideband stripper 20 should have a sufficient étendue, i.e. it should remove efficiently the sidebands for rays coming from various directions and in a sufficiently large field of view. As shown in FIG. 2, use can be made as sideband stripper of a confocal high Q-optical resonator cavity 120 made of two highly reflective concave mirrors 134 and 136 of same radii and separated by a distance equal to their radius. A confocal cavity constructed with 1 meter radius of curvature mirrors coated to produce a bandwidth of 1.5 MHz at a wavelength of 1.06 μm has an étendue of about 0.1 mm².sr, which is appropriate for most applications. Higher étendue strippers can be made by incorporating between the mirrors optical elements to correct geometrical aberrations. As shown, one of the mirrors of the confocal cavity 120 is mounted on a piezoelectric pusher 138 so that the spacing between the mirrors 134 and 136 may be varied for fine tuning. The confocal cavity 120 is optically into grated in a two-wave interferometer of Mach-Zehnder configuration comprising a beam splitter 118, a beam mixer 126 and two mirrors 124 and 128, the mirror 128 being mounted on a piezoelectric pusher 140 to vary the optical path length of one of the arms of the interferometer.

Also represented in FIG. 2 is the path of a typical skew ray 116' which shows how a large étendue is obtained. This ray is split in two rays 116'a and 116'b by the beam splitter 118. The ray 116'a enters the confocal cavity 120 and produces four series of all-superimposed rays 117' and 119' in reflection, and 121' and 122' in transmission. Only the series of rays 122' which is colinear with the incident rays 116'a is used as reference beam together with the superimposed rays 122 emerging centrally from the confocal cavity 120, which are also colinear with the incident ray 116a originating from the center ray 116. When the cavity 120 is properly tuned to the laser frequency, all sidebands located more than one cavity spectral bandwidth off the laser frequency are removed from rays 122 and 122'. These rays 122,122' are then reflected by the mirror 124 onto the beam mixer 126 where they are combined respectively with the rays 116b and 116'b which are reflected by the mirror 128 onto the beam mixer 126 after having passed through compensating elements 135 and 137. These compensating elements have the same curvatures and thicknesses as the mirrors 134 and 136 and are located at the same distance as mirrors 134 and 136 from the beam splitter 118 and the beam mixer 126, but are provided with anti-reflection coatings. When the image of the beam mixer 126 through the optical arm constituted of mirror 128, of the compensating elements 135,137 and of the beam splitter 118 is superimposed upon the image through the other optical arm which is constituted of mirror 124 and the substrates of the cavity mirrors 134 and 136, the emerging rays originating from rays 116b and 116'b are superimposed at the output on the emerging rays originating from rays 122 and 122' into rays 130 and 130', respectively, for any inclination at the input, thus providing the desired large étendue. Superposition of the images is satisfied when the optical path lengths ABC and ADC are equal and when the beam mixer 126 is oriented to bisect the angle made by the rays 116b and 122. It should be noted however that superposition of all the rays originating from an incident ray such as ray 116' is only valid in first approximation, the limitation coming from the 3rd order aberrations of the confocal cavity 120. As previously mentioned, this limitation can be removed by a more advanced cavity design, but in many cases the étendue provided by the confocal cavity 120 is sufficient. When the substrates of the cavity mirrors 134 and 136 have uniform thickness over their surfaces and are sufficiently thin, the compensating elements 135 and 137 in arm ABC can be omitted in good approximation and they thus become optional. A slight change of one of the arm length and a slight tilt of the beam mixer 26 are then required.

Two stabilization adjustments should be performed. Firstly, in order to ensure that the sidebands are completely removed from the rays emerging from the confocal cavity 120, which are used as reference beam, the laser frequency should be adjusted to the transmission peak of the cavity 120. Secondly, the Mach-Zehnder interferometric arrangement should be adjusted to the mid-fringe zero crossing for sensitive and linear detection. A setup which permits these two adjustments is shown in FIG. 3.

Figure 3:
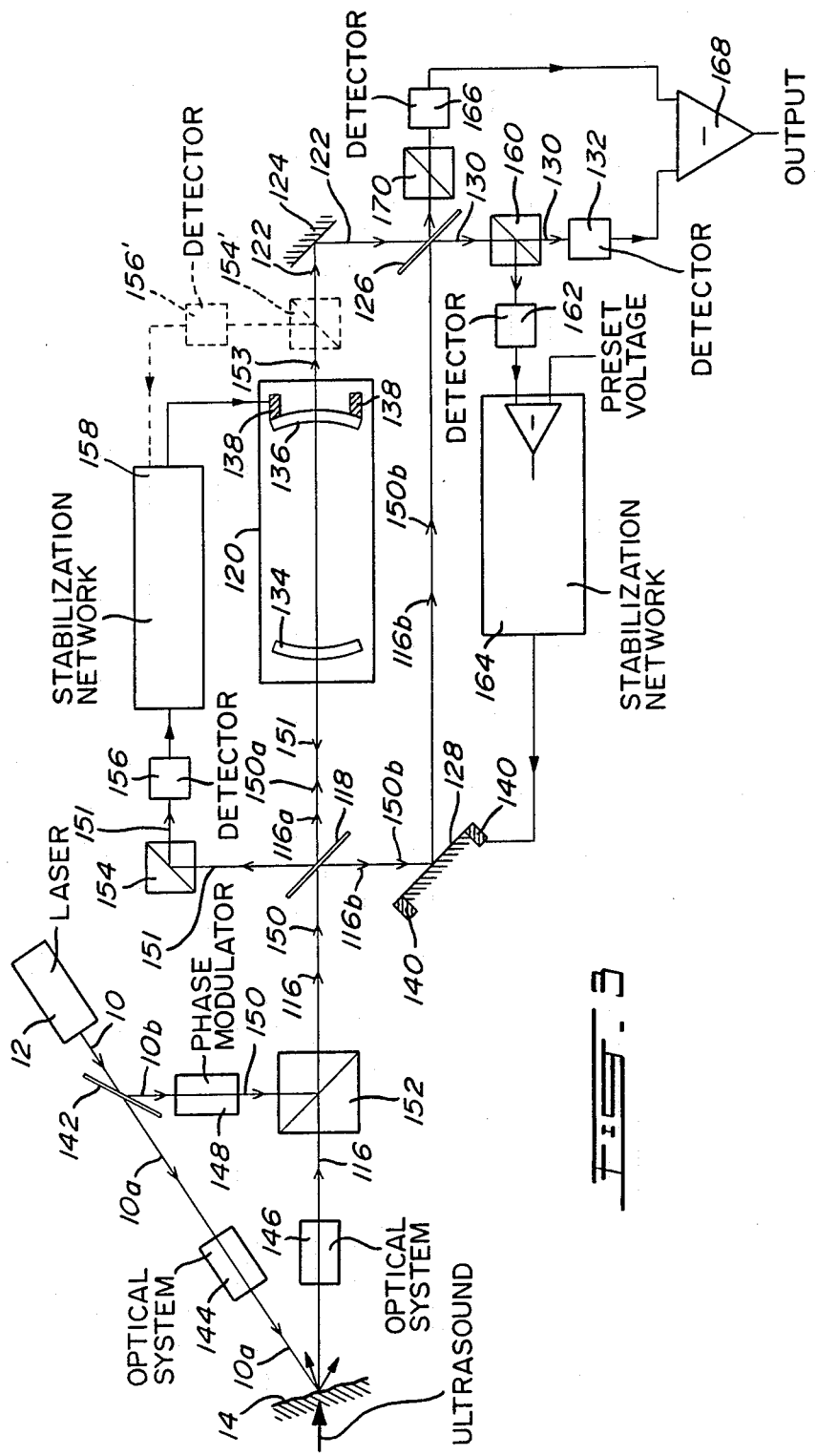
FIG. 3 schematically illustrates a first embodiment according to the invention, incorporating the interferometric arrangement shown in FIG. 2.

As shown in FIG. 3, the laser beam 10 generated by the laser source 12 is divided by a beam splitter 142 into two beam portions 10a and 10b, the beam portion 10a being directed toward the surface 14 to be probed. An appropriate optical system 144 is arranged in the optical path of the beam portion 10a to illuminate the surface 14 with a light spot of the desired size. Another optical system 146 is provided for collecting the light scattered by the surface 14. The stabilization adjustments are made possible through use of the beam portion 10b derived from the laser beam 10. The laser beam portion 10b is phase modulated by means of a phase modulator 148 using standard techniques such as the one based on the electrooptic effect, thereby providing a phase modulated stabilization beam 150 which is mixed colinearly with the scattered laser beam 116 by a polarizing beam splitter 152. A polarizing beam splitter has the property of transmitting nearly 100% of the light polarized in the plane of incidence and reflecting nearly 100% of the light polarized perpendicular to the plane of incidence. After having passed through the polarizing beam splitter 152, the scattered beam 116 is polarized in the plane of the drawing whereas the stabilization beam is polarized in a plane perpendicular thereto, and they can thus be separated from one another using other polarization optics such as polarizing beam splitters. These two beams are then sent into the Mach-Zehnder interferometric arrangement including the confocal cavity 120 illustrated in FIG. 2.

As shown, the scattered beam 116 and stabilization beam 150 are each divided by the beam splitter 118 into two beam portions 116a, 116b and 150a, 150b, the beam portions 116a and 150a entering the confocal cavity 120. The stabilization beam 151 which is partially reflected by the confocal cavity 120 is directed by the beam splitter 118 toward the polarizing beam splitter 154 which reflects it onto the stabilization detector 156. The detector 156 detects a signal varying at the frequency of the phase modulator 148, which is transmitted to a stabilization network 158 for the confocal cavity 120. The method described by R.W.P. Drever et al in Applied Physics B, Vol. 31, (1983), pp. 97–105 can be used to stabilize the laser cavity from its reflection side. According to this method, a null signal at the modulation frequency is automatically tracked so that the laser frequency corresponds to the cavity resonance frequency. A correction signal generated by the stabilization network 158 is applied to the piezoelectric pusher 138 so as to change the distance between the mirrors 134 and 136 and thus change the cavity resonance frequency. Alternatively, it is possible to work on the transmission side of the confocal cavity 120 using the polarizing beam splitter 154' and stabilization detector 156' shown in broken lines; the transmitted stabilization beam 153 is separated from the reference beam 122 emerging from the cavity 120 and derived from the scattered beam 116 by means of the polarizing beam splitter 154' which reflects the stabilization beam 153 onto the detector 156'The stabilization network 158 tracks a null signal at the modulation frequency as in the above-described method of stabilization from the reflection side of the confocal cavity 120.

Stabilization of the Mach-Zehnder configuration is realized by selecting one of the stabilization beams originating from the interference of beams 150b and 153 and emanating at the output from the beam mixer 126, using the polarizing beam splitter 160 which is optically coupled to the stabilization detector 162. The stabilization network 164 automatically tracks a zero of the second harmonic of the modulation frequency corresponding to a zero of the second derivative of the response curve of the Mach-Zehnder interferometer. Alternatively, as shown in FIG. 3, the stabilization network 164 generates an error signal by comparing the DC voltage output of the detector 162 to a preset voltage value corresponding to the mid-fringe zero crossing level. A correction signal generated by the stabilization nework 164 is then applied to the piezoelectric pusher 140 so as to move the mirror 128 and thus change the optical path length of one of the arms of the Mach-Zehnder interferometer arrangement.

As shown in FIG. 3, two detectors 132 and 166 are used at the output and are followed by a differential amplifier 168, the polarizing beam splitter 170 like the polarizing beam splitter 160 preventing the stabilization beams 150b and 153 from reaching the detectors 132 and 166. Such an arrangement permits to double the output signal and to diminish the effect of the fluctuations of the laser amplitude on the signal as well as the effect of non-interferring beam 121'.

Figure 4:
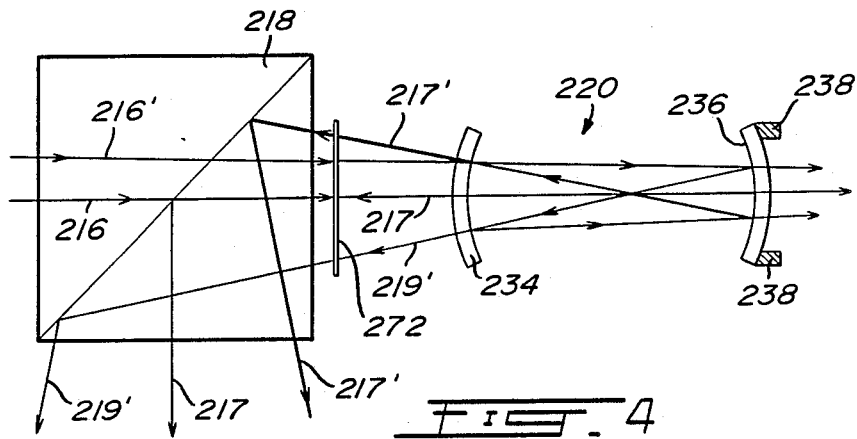
FIG. 4 is a schematic diagram illustrating the use of a confocal cavity in reflection mode as a sideband stripper, without any external interferometric arrangement.
Figure 5:
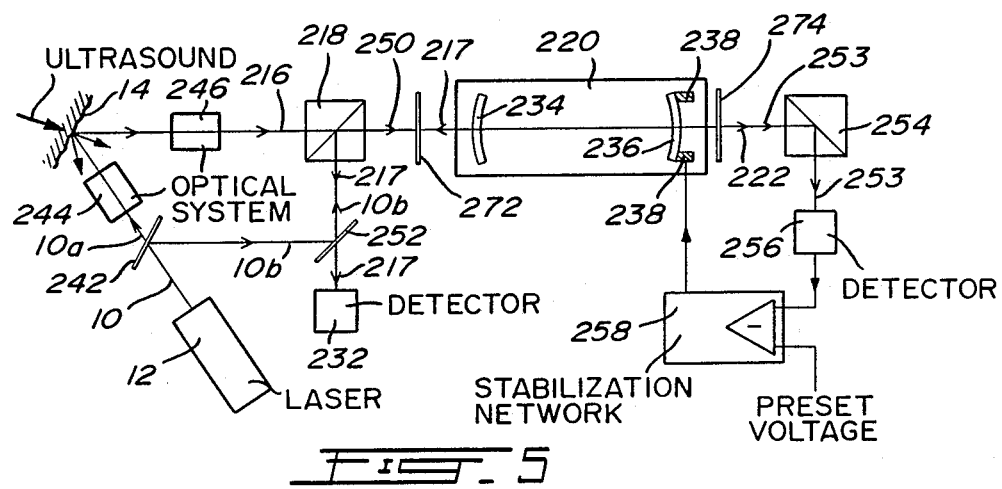
FIG. 5 schematically illustrates a second embodiment according to the invention, incorporating the optical arrangement shown in FIG. 4.

Turning now to FIGS. 4 and 5 which illustrate a second embodiment according to the invention, use is made only of a confocal cavity 220 without any external interferometric arrangement. As shown, instead of using an ordinary beam splitter 118 as in the embodiment illustrated in FIGS. 2 and 3, a polarizing beam splitter 218 is used, which is followed by a quarter-wave plate 272 oriented at 45° with respect to the incident polarization. FIG. 4 illustrates the optical paths followed by a center ray 216 as well as by a skew ray 216' similarly as in FIG. 2. The embodiment of FIG. 4 is based on the fact that the electromagnetic field of the reflected beam 217' emerging from the cavity 220 is actually the superposition of a field directly reflected by the mirror 234, which includes the carrier laser frequency and adjacent sidebands, and a field leaking off the cavity in which the sidebands have been filtered out and which corresponds to the reference beam. This superposition occurs for any orientation of the incident ray (at least in first approximation), providing the desired large étendue. This superposition also applies to the reflected beam 217 emerging from the cavity, which is derived from the center ray 216.

Coupling of the beams in and out of the confocal cavity 220 is provided by the polarizing beam splitter 218 and quarter-wave plate 272. The beams 216,216' after having passed through the polarizing beam splitter 218 are polarized in the plane of the drawing and are transmitted to the confocal cavity 220 as circularly polarized beams by the quarter-wave plate 272 oriented at 45°. After reflection and transmission again through the quarter-wave plate 272, the reflected beams 217,217' become polarized in a plane perpendicular to the plane of the drawing and are then reflected by the polarizing beam splitter 218. In practice, the beam 219' leaking off the cavity 220 cannot be separated on the detector 232 (shown in FIG. 5) from superposition beams 217 and 217' if the laser beam received from the probed surface 14 is well centered on the cavity axis. The beams 217' and 219' add incoherently (i.e. intensities are simply added) on the detector 232. Theory and experiment confirm that this is not detrimental and actually tend to flatten further the frequency response for frequencies of the order of the cavity bandwidth. Theory and experiment also show that the laser frequency should be stabilized on the slope of a resonance peak, somewhere around half resonance height. Stabilization at resonance gives two contributions from the sidebands which cancel each other. In this embodiment, it is not possible to change the phase of the reference beam with respect to the beam scattered by the surface 14 and having sidebands independently from the adjustment for filtering.

A suitable configuration for stabilizing the confocal cavity 220 to the laser frequency is shown in FIG. 5. The laser beam 10 generated by the laser source 12 is divided by the beam splitter 242 into two beam portions 10a and 10b, the beam portion 10a being directed toward the surface 14 to be probed. An optical system 244 is arranged in the optical path of the beam portion 10a to illuminate the surface 14 with a light spot of the desired size. Another optical system 246 is provided for collecting the light scattered by the surface 14. The stabilization adjustment is made possible through use of the beam portion 10b derived from the laser beam 10. The laser beam portion 10b is reflected by a beam splitter 252 onto the polarizing beam splitter 218 to provide a stabilization beam 250 which is mixed colinearly with the scattered laser beam 216. The superposition beam 217 reflected by the confocal cavity 220 is reflected by the polarizing beam splitter 218 and then transmitted through the beam splitter 252 onto the signal detector 232. This arrangement permits separation of the reflected beam 217 from the stabilization beam reflected by the cavity, the latter beam being transmitted toward the surface 14 and not onto the detector 232. A second quarter-wave plate 274 is arranged after the confocal cavity and has its axis antiparallel to the axis of the first quarter-wave plate 272 so that the combination of both has no polarization effect. Such an arrangement enables the transmitted stabilization beam 253 to be reflected by the polarizing beam splitter 254 onto the stabilization detector 256, without being affected by the beam 222 emerging from the cavity 220 and derived from the scattered beam 216. The mirror 236 of the confocal cavity 220 is highly reflecting with transmission of the order of 0.1% in order to give best detection conditions. Stabilization can be performed easily by comparing the DC voltage output of the detector 256 to a preset voltage value corresponding approximately to half resonance peak height. A correction signal generated by the stabilization network 258 can then be applied to the piezoelectric pusher 238 so as to change the distance between the mirrors 234 and 236 and thus change the cavity resonance frequency.

Figure 6:
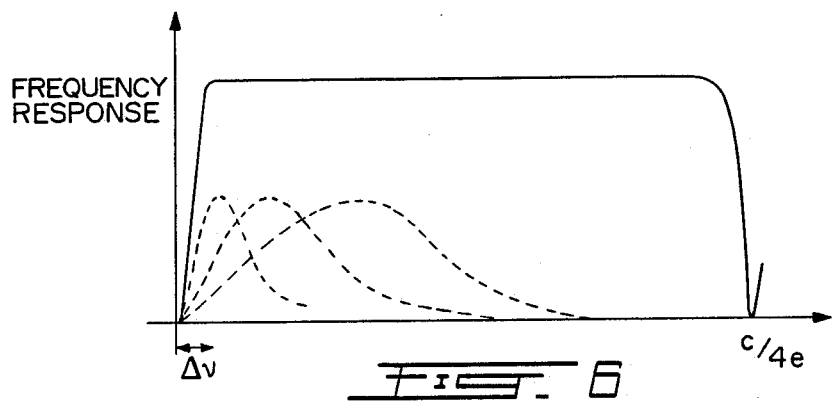
FIG. 6 is a graph illustrating the frequency response which is typically obtained in accordance with the invention.

A typical frequency response curve obtained in accordance with the invention is shown in FIG. 6, where $\Delta \nu$ is the bandwidth at half maximum. The curves shown in broken lines are illustrative of the results obtained according to prior art techniques, such as disclosed in U.S. Pat. No. 4,659,224. As shown, the invention enables to obtain a frequency response which is flat between $\simeq \Delta \nu$ and $c/4e - \Delta \nu$, where c is the speed of light and e is the cavity spacing and mirror radius. For example, in the case of the second embodiment illustrated in FIGS. 4 and 5, for a 1 meter long cavity 220 with mirrors 234,236 reflecting close to 100% and 94% (bandwidth $\simeq 1.5$ MHz), the response is flat between 1.5 MHz and 73.5 MHz. For nonabsorbing and nonscattering coatings on the mirrors, a situation which can now be obtained by advance coating technology, calculations show that the responsivity and the signal-to-noise ratio are larger for both embodiments than those obtained in the previous art configuration. In the case of the second embodiment where mirror 236 is 100% reflecting (no transmission), the signal magnitude is about 4 times the peak magnitude obtained with previous art configuration and the signal-to-noise ratio for photon noise limited detection is about twice as much.

Although the method and systems described above are meant to be used primarily for the detection of the transient motion of surfaces of solid bodies, they can also be used to detect density or pressure fluctuations affecting the gas or air path between a laser source and a receiver. The optical detection technique described is particularly useful for detecting the high frequency components of these fluctuations.

I claim:

1. A method of optically detecting transient motion from a scattering surface, which comprises the steps of:
    (a) directing a laser beam having a predetermined frequency onto said surface to thereby scatter said laser beam and produce a scattered laser beam defining an optical wavefront and having an optical spectrum with a central peak at said predetermined frequency and a sideband on either side of said central peak;
    (b) causing the laser beam scattered by the surface to interfere with a reference beam derived from the scattered laser beam and having an optical wavefront substantially matching the wavefront of said scattered beam and an optical spectrum with a single peak at said predetermined frequency and no sidebands, to obtain an optical signal; and
    (c) detecting said optical signal and converting same into an electrical signal representative of the transient motion.

2. A method as claimed in claim 1, wherein step (b) is carried out by dividing said scattered laser beam into first and second scattered beam portions each having an optical spectrum with said central peak and said sidebands, removing the sidebands from said second scattered beam portion to obtain a sideband-free beam portion defining said reference beam, and combining said first scattered beam portion with said reference beam to cause interference thereof and thereby provide said optical signal.

3. A method as claimed in claim 2, wherein the sidebands are removed from said second scattered beam portion by passing said second scattered beam portion through an optical resonator cavity having a reflection side and a transmission side such that the beam portion emerging from the transmission side of said resonator cavity has an optical spectrum with a single peak at said predetermined frequency and no sidebands.

4. A method as claimed in claim 3, wherein said optical resonator cavity is a cavity of confocal type which is optically integrated in a two-wave interferometer of Mach-Zehnder configuration having two optical arms and including beam splitting means and beam mixing means arranged to provide superimposed rays emerging from said beam mixing means.

5. A method as claimed in claim 4, wherein said scattered laser beam is divided into said first and second scattered beam portions by a beam splitter, said first scattered beam portion is reflected by a first mirror to a beam mixer, and wherein said second scattered beam portion is passed through said confocal-type cavity and the beam portion emerging from the transmission side of said confocal-type cavity is reflected by a second mirror onto said beam mixer where it is combined with the first scattered beam portion reflected by said first mirror.

6. A method as claimed in claim 4, wherein aid confocal-type cavity has a cavity resonance frequency which is adjusted to said predetermined frequency and wherein said mach-Zehnder configuration has an optical path difference which is adjusted to mid-fringe zero crossing level.

7. A method as claimed in claim 6, wherein the cavity resonance frequency of said confocal-type cavity and the optical path difference of said Mach-Zehnder configuration are adjusted by means of a phase-modulated stabilization beam which is derived from said laser beam and mixed with said scattered laser beam prior to input into said Mach-Zehnder configuration.

8. A method as claimed in claim 1, wherein step (b) is carried out by sending said scattered laser beam into an optical resonator cavity having a reflection side on which said scattered laser beam is incident and having an opposite transmission side, whereby said scattered beam upon entering said optical resonator cavity is divided into a reflected beam portion and a transmitted beam portion each having an optical spectrum with said central peak and said sidebands, said transmitted beam portion emerging from the reflection side of said optical resonator cavity as a sideband-free beam portion defining said reference beam, which is combined with said reflected beam portion to cause interference thereof and thereby provide said optical signal.

9. A method as claimed in claim 8, wherein said optical resonator cavity is a cavity of confocal type.

10. A method as claimed in claim 9, wherein said confocal-type cavity exhibits a cavity resonance transmission peak having two slopes and comprises first and second movable, concave mirrors of same radii spaced from one another by a distance equal to their radius, and wherein said first and second mirrors are moved relative to one another to vary the spacing therebetween and to thereby change the position in frequency of said cavity resonance transmission peak.

11. A method as claimed in claim 10, wherein said cavity resonance transmission peak is adjusted with respect to said predetermined frequency such that said predetermined frequency is located on either slope of said cavity resonance transmission peak.

12. An apparatus for optically detecting transient motion from a scattering surface, which comprises:
    laser source means for generating a laser beam having a predetermined frequency and directing same onto said surface to thereby scatter said laser beam and produce a scattered laser beam defining an optical wavefront and having an optical spectrum with a central peak at said predetermined frequency and a sideband on either side of said central peak;
    optical assembly means for deriving from the scattered laser beam a reference beam having an optical wavefront substantially matching the wavefront of said scattered beam and an optical spectrum with a single peak at said predetermined frequency and no sidebands, and for causing the scattered laser beam to interfere with the reference beam so as to obtain an optical signal; and
    detector means for detecting said optical signal and converting same into an electrical signal representative of said transient motion.

13. An apparatus as claimed in claim 12, wherein said optical assembly means comprises beam splitting means for dividing said scattered laser beam into first and second scattered beam portions each having an optical spectrum with said central peak and said sidebands; sideband stripping means for removing the sidebands from said second scattered beam portion to obtain a sideband-free beam portion defining said reference beam; and beam mixing means for combining said first scattered beam portion with said reference beam to cause interference thereof and thereby provide said optical signal.

14. An apparatus as claimed in claim 13, wherein said sideband stripping means comprises an optical resonator cavity having a reflection side and a transmission side.

15. An apparatus as claimed in claim 14, wherein said optical resonator cavity is a cavity of confocal type having a cavity resonance frequency, said confocal-type cavity being optically integrated in a two-wave interferometer of Mach-Zehnder configuration having two optical arms and including said beam splitting means and said beam mixing means, and wherein said beam splitting means and beam mixing means are arranged to provide superimposed rays emerging from said beam mixing means.

16. An apparatus as claimed in claim 15, wherein said interferometer further includes a first mirror for reflecting said first scattered beam portion to said beam mixing means and a second mirror for reflecting the reference beam emerging from the transmission side of said confocal-type cavity to said beam mixing means.

17. An apparatus as claimed in claim 16, wherein said first and second mirrors are movable relative to one another to vary the optical path lengths of the interferometer arms.

18. An apparatus as claimed in claim 15, wherein said confocal-type cavity comprises a pair of concave mirrors of same radii spaced from one another by a distance equal to their radius, said mirrors being movable relative to one another to vary the spacing therebetween and to thereby change said cavity resonance frequency.

19. An apparatus as claimed in claim 18, further including first stabilization adjustment means for adjusting the cavity resonance frequency of said confocal-type cavity to said predetermined frequency, and second stabilization adjustment means for adjusting the Mach-Zehnder configuration to midfringe zero crossing level.

20. An apparatus as claimed in claim 12, wherein said optical assembly means comprises an optical resonator cavity having a reflection side for receiving said scattered laser beam and having an opposite transmission side.

21. An apparatus as claimed in claim 20, wherein said optical resonator cavity is a cavity of confocal type.

22. An apparatus as claimed in claim 21, wherein said confocal-type cavity comprises first and second concave mirrors of equal radii spaced from one another by a distance equal to their radius, said first mirror defining beam splitting/mixing means for dividing said scattered laser beam into a reflected beam portion and a transmitted beam portion each having an optical spectrum with said central peak and said sidebands such that the beam portion transmitted by said first mirror into said confocal-type cavity is subjected to a multiple reflection within said confocal-type cavity and emerges from the reflection side thereof as a sideband-free beam portion defining said reference beam, and for combining said reflected beam portion with said reference beam to cause interference thereof and thereby provide said optical signal.

23. An apparatus as claimed in claim 22, further including a polarizing beam splitter optically coupled with said confocal-type cavity for transmitting said scattered laser beam to said confocal-type cavity and for reflecting the combined beams emerging from the reflection side of said confocal-type cavity to said detector means.

24. An apparatus as claimed in claim 22, wherein said confocal-type cavity exhibits a cavity resonance transmission peak having two slopes and wherein said first and second mirrors are movable relative to one another to vary the spacing therebetween and to thereby change the position in frequency of said cavity resonance transmission peak.

25. An apparatus as claimed in claim 24, further including stabilization adjustment means for adjusting said cavity resonance transmission peak with respect to said predetermined frequency such that said predetermined frequency is located on either slope of said cavity resonance transmission peak.

* * * * *